United States Patent [19]

Nehring

[11] Patent Number: 4,489,750
[45] Date of Patent: Dec. 25, 1984

[54] PRESSURE OPERATED PULSATILE FLUID FLOW DEVICE

[75] Inventor: John R. Nehring, East Greenwich, Conn.

[73] Assignee: Davol, Inc., Cranston, R.I.

[21] Appl. No.: 296,066

[22] Filed: Aug. 25, 1981

[51] Int. Cl.³ .................. F16K 31/12; F16K 15/14
[52] U.S. Cl. ............................. 137/496; 137/853; 137/624.14; 239/99
[58] Field of Search ............... 137/496, 843, 852, 853, 137/624.14, 469; 251/5; 239/99, 101

[56] References Cited

U.S. PATENT DOCUMENTS

| | | | |
|---|---|---|---|
| 2,662,485 | 12/1953 | Ilfrey | 137/853 X |
| 2,684,049 | 7/1954 | Hollis | 137/853 X |
| 2,993,654 | 7/1961 | Norton | 137/853 X |
| 3,416,567 | 12/1968 | Von Dardel et al. | 137/853 X |
| 3,448,766 | 6/1969 | Schule | 137/853 X |
| 3,702,141 | 11/1972 | Wetterhorn | 137/469 |
| 3,965,934 | 6/1976 | Rosenberg | 137/624.14 |
| 4,111,391 | 9/1978 | Pilolla | 251/5 |
| 4,290,454 | 9/1981 | Shetler | 137/853 |
| 4,300,748 | 11/1981 | Kreeley | 251/5 |
| 4,313,699 | 2/1982 | Steele | 137/853 X |

FOREIGN PATENT DOCUMENTS

| | | | |
|---|---|---|---|
| 1475954 | 8/1969 | Fed. Rep. of Germany | 137/853 |
| 1946833 | 5/1970 | Fed. Rep. of Germany | 137/853 |
| 2149627 | 4/1972 | Fed. Rep. of Germany | 137/853 |
| 2522069 | 11/1976 | Fed. Rep. of Germany | 137/853 |
| 1020359 | 2/1966 | United Kingdom | 137/853 |

Primary Examiner—Alan Cohan
Assistant Examiner—John A. Rivell
Attorney, Agent, or Firm—Wolf, Greenfield & Sacks

[57] ABSTRACT

Pulsations are created in a fluid flow stream by a pulsatile device. The device includes a flexible, resilient element which oscillates under the influence of a pressure differential to interrupt the fluid flow at regular intervals, thereby causing the outlet flow to pulsate. The device may be connected directly to a supply of fluid under pressure.

6 Claims, 14 Drawing Figures

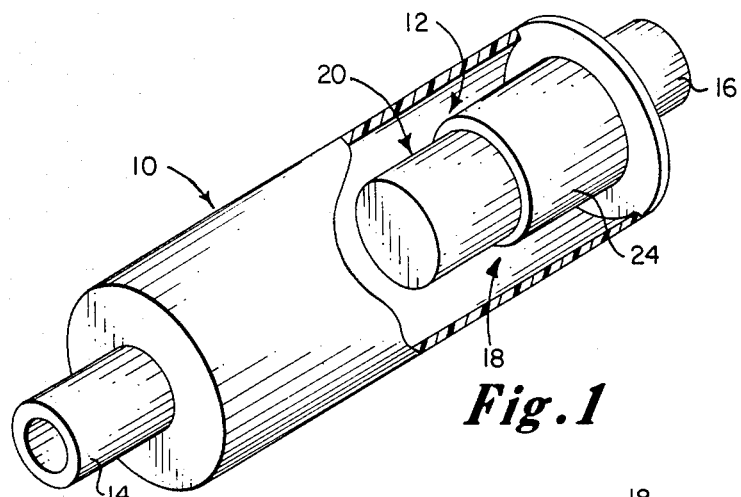
*Fig. 1*
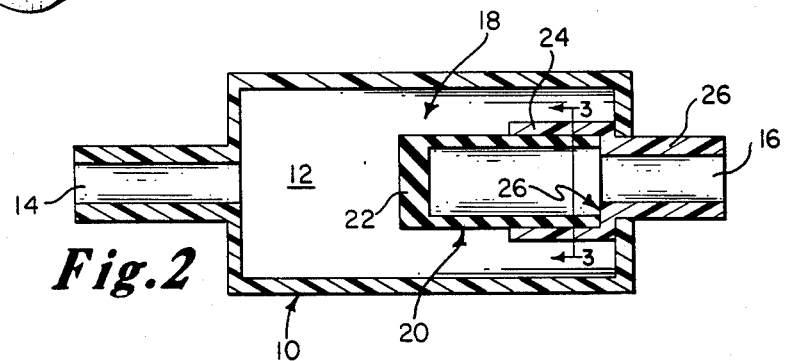
*Fig. 2*
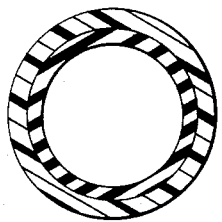  
*Fig. 3*            *Fig. 5*
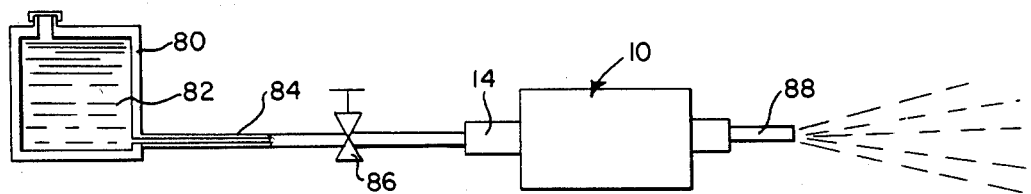
*Fig. 12*

PRESSURE OPERATED PULSATILE FLUID FLOW DEVICE

BACKGROUND OF THE INVENITON

This invention relates to fluid flow system, and particularly a device used in such systems to cause the fluid to pulsate.

Various devices for causing pulsatile fluid flow have been known and have found increasing use in a variety of environments, and, for example, are used in medical and dental environments. Pulasting fluid jets are highly effective in surgical environments, such as to remove surgical debris from the surgical site. The use use of pulsating fluid jets has been demonstrated to a very effective way of cleaning wounds or applying antibiotics, disinfectants and the like. The effectiveness of the pulsating fulid technique is the result of the repeated flexure if tissue and/or repeated dynamic impact from the pulsations which tends to materially assist in working loose of dirt particles or other debris. Pulsating fluid devices also have been used in pre-operation cleaning, such as by pre-scrubbing by surgeons. It has been reported that such pre-scrubbing with water jets is more effective in removing bacteria than the usual five-minute hand scrub.

Pulsating water flow devices also have been available for some time for use in connection with dental and oral hygiene and maintenance to remove food particles from difficult to reach crevices as well as to stimulate and massage gums and oral tissue.

Pulsating jet devices also have been used for their pulsating or massaging effect, such as in shower heads, as well as in various therapeutic systems utilizing water or fluid massage.

In general, the various pulsation flow systems which have been available, utilize intermittent pumping devices of some complexity. Typically, the device requires a pump mechanism which is driven by any of a variety of motors. The pump and motor systems may be electrically operated or, in some instances, may be operated in response to the fluid pressure and flow of the fluid which is to be pulsated. In general, the electric motor-powered system tends to be more prevalent where the device is to be used in a medical or dental environment whereas the water pressure operated system appears to be more commonly used in shower heads and the like.

While a number of devices which utilize a pulsatile flow device have enjoyed varying degrees of commercial success they still are not free from difficulties. For example, they tend to be somewhat cumbersome and are not as portable as would be desired. Thus, while it might be quite satisfactory for an oral hygiene device to remain in place, for use at a fixed location where both water and electricity is available, the device does not lend itself to portability, as might be desired by a traveller. When a fluid pulsatile device is used in a surgical or operating room environment, it is preferable that it be as small, as compact and as light as is reasonably possible. While it would be desirable to have a prepackaged, presterilized disposable device, none has been available to date.

It is among the primary objects of the invention to provide an improved and greatly simplified fluid pulsatile device.

SUMMARY OF THE INVENTION

The present invention concerns a pulsatile device which may be interposed in the fluid flow path, and which causes the flow to pulsate in response to a pressure differential across the device. The pressure differential may be caused by the pressure of the fluid in the flow path. The device includes a housing having an inlet which is connected to the pressured fluid source and an outlet which emits the fluid in pulsations. The flow path through the housing normally is obstructed by a flexible, resilient valve element, which is the only moving part in the device. The valve element is shaped and supported in the housing in a manner such that it will respond to a differential pressure across the element, such as an increased upstream pressure or a reduced downstream pressure, or a combination of both. The valve element is constructed so that when the pressure differential reaches a predetermined triggering level (the "trigger pressure"), the valve element will abruptly snap open and enable fluid to flow past the element. The fluid flow causes a drop in the static pressure differential across the valve element and when the pressure differential drops to a predetermined value (the "reset pressure") the resilient valve element returns to its monostable, flow-obstructing condition. As the fluid flow terminates, the pressure differential again builds up across the valve element until the trigger pressure is reached again which causes the valve element to snap open again to initiate another cycle. This repeated cycling in response to differential pressures at an elevated "triggering" level and lowered "reset" level causes the device to oscillate between its stable closed position and its unstable open position, thereby causing pulsations in the fluid flow.

As will be described below in further detail, the valve element of illustrative embodiments of the invention are in the form of a hollow flexible, resilient, elastic cylinder which is closed at one end and open at the other end. The open end of the cylinder is more easily flexed or collapsed radially than at the closed end. The cylinder is supported so that its open end extends into a rigid tubular holder. The tubular holder also leads to or itself defines part of, the outlet port. The closed end of the elastic cylinder is located upstream of and extends out of the tubular holder. The periphery of the cylinder and configuration of the tubular holder are such that the open end of the cylinder fits in a slight interference fit within the tubular holder. The slight interference fit is sufficient to effect a substantial seal between the periphery of the elastic cylinder and the surface of the tubular holder.

In operation, as the pressure differential builds up across the valve element (e.g., increased pressure on the upstream side), the cylindrical sidewall of the elastic element begins to dimple and collapse radially. The seal between the elastic element and the holder remains in effect until a predetermined triggering pressure differential is reached at which time the elastic cylindrical sidewall snaps into a collapsed configuration, thereby instantaneously disrupting the seal and defining a flow path through the holder, past the collapsed elastic element. Immediately upon establishment of fluid flow past the disrupted seal, the static pressure differential acting on the elastic element begins to drop and reaches a reduced reset level at which the resilient cylindrical valve element under the influence of its inherent resilience, snaps back into its sealed configuration within the tubular holder. Immediately upon such resealing, the pressure differential across the element begins to increase toward the triggering level. Thus, the pressure differential acting on the elastic element will cause the sidewall of the cylindrical element alternately to collapse and reset which, in turn, causes the intermittent pulsating fluid flow.

In addition to its action as a pulsatile device, the invention also may serve as a check valve, to prevent reverse flow, depending on the precise nature of the fluid system in which the device is used. In still another mode of operation, the device can be used as a pressure responsive, pulsable relief valve to control the degree of vacuum or pressure in a vessel or other fluid system requiring pressure limiting controls.

It is among the general objects of the invention to provide a new and improved pulsatile flow device.

Another object of the invention is to provide a pulsatile flow device which is inexpensive to manufacture and lends itself to one-time, disposable use;

Another object of the invention is to provide a pulsatile flow device which has only a single moving part and which is substantially maintenance free.

A further object of the invention is to provide a pulsatile flow device which may be easily connected to existing fluid flow lines to cause the line to deliver a pulsed flow.

Another object of the invention is to provide a pulsatile flow device of extreme simplicity.

A further object of the invention is to provide a pulsating flow device which occupies minimal space and lends itself to portability.

Another object of the invention is to provide a device of the type described which is operable over a very wide range of pressures.

Another object of the invention is to provide a pulsatile flow device which requires no electric motors, or other rotating parts and which operates entirely in response to a differential pressure across the device.

A further object of the invention is to provide a device of the type described which also is usable as a check valve, to prevent reverse flow in the fluid system.

Still another object of the invention is to provide a device of the type described which can be pulsed intermittently to control pressures in a fluid system.

DESCRIPTION OF THE DRAWINGS

The foregoing and other objects and advantages of the invention will be appreciated more fully from the following further description thereof, with reference to the accompanying drawings wherein:

FIG. 1 is a broken-away diagrammatic illustration of a device including a chamber which embodies the pulsatile element of the invention;

FIG. 2 is a longitudinal sectional illustration of the device shown in FIG. 1;

FIG. 3 is a sectional elevation of the device as seen along the line 3—3 of FIG. 2;

FIG. 5 is an illustration of the valving element in its collapsed configuration as seen along the line 5—5 of FIG. 4;

FIG. 12 is a diagrammatic illustration of a device of the type shown in FIG. 1 connected to a source of liquid under pressure.

DESCRIPTION OF ILLUSTATIVE EMBODIMENTS OF THE INVENTION

Figure 4:
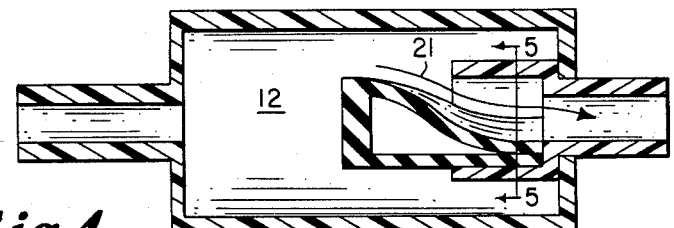
FIG. 4 is an illustration similar to FIG. 2 illustrating configuration of the valving element in its collapsed configuration.

FIG. 1 illustrates, somewhat digrammatically, a device which incorporates the principles of the invention. The device includes a housing 10 which defines a chamber 12. The housing includes an inlet 14 and an outlet 16. The inlet 14 may be connected, by a tube or the like, to a source of fluid under pressure. The outlet 16 may be connected to a tube or directly to a nozzle or the like.

The housing 10 itself may be considered as defining a portion of a fluid flow path extending from the inlet 14 to the outlet 16. Located along that flow path is one embodiment of a valving arrangement, indicated generally by the reference character 18, which generates the pulsatile flow in accordance with the invention. The valving arrangement 18 is in the form of a hollow tubular (preferably cylindrical) element 20 which is closed at one end (its upstream end) by the end wall 22 and is open at its other, (downstream) end. The valving element 20 is flexible and resilient and, for example, may be made from latex rubber.

The open, downstream end of the cylindrical valve element 20 is received in and is supported by a tubular holder 24 which is mounted in the housing 10 so as to be in communication with the outlet 16. As shown, the holder 24 may be formed integrally with an outlet tube 26 which defines the outlet 16. The holder 24 is provided with a shoulder 28. The cylindrical valve element 20, when properly disposed within the holder 24, will have a substantial portion of its closed end projecting out of the holder 24 (as will be described more fully below) and its open end will be disposed in close proximity to the shoulder 28.

The closed end of the tubular element 20 is constructed to assure that it will not collapse longitudinally under the influence of fluid pressures within the device. Thus, the end wall 22 may be made slightly thicker than the remaining portions of the element 20 so as to define a relatively rigid portion of the element. It may be noted that although the end wall is illustrated as being flat and at right angles to the longitudinal axis of the cylinder, the shape of the outer closed end of the valve element need not be squared as shown. It may be bullet-shaped, or otherwise shaped as long as the closed end is sufficiently rigid and resistant to longitudinal, axial collapse.

The outer diameter of the elastic cylindrical element 20 and the inner diameter of the holder 24 are selected to provide a slight interference fit. The slight interference fit assures that the seal will be full and effective when the element is in its sealed, uncollapsed configuration. The interference fit also aids in assuring that the valve element 20 will remain in place and will not shift about within the holder, although other means also may be provided to assure that the valve element will remain properly located within the holder 24.

In the embodiment shown in FIG. 2, the valve element 20 normally is held in place within the holder 24 by the axial pressure acting on the end wall 22 of the element, which tends to maintain and urge the element 20 to a fully seated position within the holder 24, in which the free end of the element 20 rests against the shoulder 28 at the end of the holder 24. In some instances, it may be desired to help retain the element by a small dab of cement (not shown) applied in a single location at the interface of the outer surface of the element 20 and the inner surface of the holder 24. As will be apparent from the further description of the invention, adhesive should be used in a small quantity and at a location which will not interfere with the flexure and oscillation of the element 20.

The elastic cylindrical element 20 and holder 24 are arranged so that when the device is connected to a source of fluid under pressure, the pressure in the chamber 12 will reach a predetermined level, referred to herein as the triggering pressure, which will cause the valve element 20 to collapse along its sidewall, as suggested in FIGS. 4 and 5. As the sidewall collapses to the configuration shown in FIGS. 4 and 5, it opens a flow path from the chamber 12 through the outlet 16 as indicated by the arrow 21. As soon as the fluid begins to flow, the static pressure in the chamber 12 and the differential pressure across the element 20 begins to drop. The valving arrangement 18 is constructed so that when a predetermined lower static pressure (reset pressure) has been reached, the collapsing force on the element 20 will no longer be sufficient to maintain it in its collapsed state, and the element will return to its expanded cylindrical shape under the influence of its inherent resilience, thereby shutting off the fluid flow. With the valve element 20 returned to its stable, closed position, the fluid pressure within the chamber 12 immediately builds up to the triggering pressure which, when reached, will again collapse the cylindrical element to begin a new pulse of fluid flow through the outlet 16. The cycle repeats continuously and automatically, as long as a sufficient level of pressure is maintained within the chamber 12, as will be the case when the device is connected to the fluid pressure source.

Figure 6:
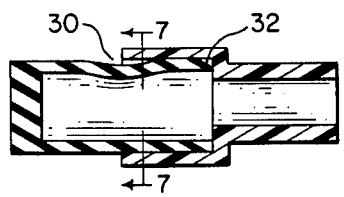
FIG. 6 is a sectional elevation of the valve element and its holder illustrating the dimpling of the valve element as the valve element approaches the point at which it will snap to an open configuration.
Figure 7:
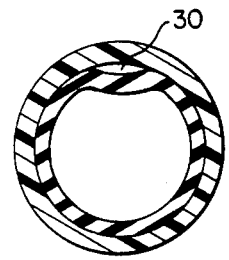
FIG. 7 is a sectional illustration of the device as seen along the line 7—7 of FIG. 6.

The flow opening action of the valving element is substantially instantaneous. The flow closing action of the valve element, however, may be varied from substantially instantaneous to relatively slow, depending on a number of factors such as the fluid flow rate into the housing as well as the extent of flow restrictions which may be associated with the outlet. FIGS. 6 and 7 suggest diagramatically the manner in which the element 20 responds as pressure differential builds up and acts on it. When the element 20 is in its uncollapsed, sealed configuration (FIGS. 2 and 3), the pressure differential resulting from a higher upstream pressure applies an axial pressure on the element 20 tending to maintain the element fully and firmly seated in the holder 24 while at the same time applying a circumferential force fully about the exposed portion of the cylindrical sidewall of the element 20. The sidewall, which is more flexible because of its shape, thickness and unsupported free end, begins to form a dimple (indicated at 30 in FIGS. 6 and 7) of progressively increasing depth and width in response to the progressively increasing pressure differential. The dimple 30 may start at any location about the circumference of the element 20. As the dimple approaches the free, outermost end 32 of the element 20, the seal between the tubular element 20 and the inner surface of the holder 24 breaks which enables fluid to rush past.

The action of the valve element 20, as it moves from its sealed to an unsealed configuration, is substantially instantaneous. In that regard, it should be noted that the valve element 20 remains sealed at its outermost end 32 even during expansion of the diameter of the dimple 30, until the size of the dimple 30 approaches the outer end 32 of the tubular element. The seal thus is maintained until the outermost end 32 of the tubular element 20 separates from its intimate contact with the inner surface of the holder. When the seal between end 32 of the tubular element 20 and the inner surface of the holder 24 does break, it does so with a toggle-like, snap action which is substantially instantaneous. The toggle-like snap action of the valve element 20 may be appreciated from a comparison of FIGS. 3 and 5 from which it can be seen that the upper portion of the tubular element 20 must shift from a downwardly opening arc to an upwardly opening arc, all within the confines of the fixed diameter cylindrical holder 24. This necessitates somewhat of a snapping, toggle-like action when the seal breaks at the free inner end 32 of the element 20.

The characteristics and parameters of the fluid flow and resulting pulsations may be varied by varying certain parameters and characteristics of the device. For example, the frequency of the pulsations, the pressure at the outlet, the fluid flow rate, and the volume of fluid per pulse may be varied to suit the particular intended use and environment for the device. Among the variables in the device which can be utilized to control its pulsating and flow characteristics so as to render it suitable for use in a particular environment include the selection of the material for the element 20 as well as variation in the relative dimensions of the valve element 20 and the holder 24. The diameter of the outlet 16 also has an effect on the operating characteristics of the device, in that a narrower outlet tends to increase the frequency of pulsations.

By way of example, I have found a very satisfactory range of pulsating frequencies and flow rates to result from an arrangement in which the length of the elastic element 20 is approximately four times its inner diameter and with an amount equal to about two times the inner diameter being contained within the holder, a wall thickness for the cylindrical element being approximately one-fifth of the inner diameter, with the elastic element being made from natural latex rubber having a durometer of 40 (A scale). I have found a device having these characteristics to operate quite adequately in a frequency range of about 800 to 1200 pulses per minute under the influence of between 15 PSI–100 PSI inlet pressure. A frequency of the order of 800–1200 pulses per minutes appears to be commonly used in a number of applications, such as oral hygiene devices.

Also among the advantages of the invention is that it may be used over a wide range of pressures. For example, the device can be operated with source fluid pressures of up to 5000 psi depending on the specific dimensional parameters selected for the device and the selection of resilient material for the valve element 20. The range of frequencies can be quite wide, for example as low as 20 to over 3000 cycles per minute. The frequency of operation may be varied for a given pressure by throttling the upstream flow, for example at the inlet 14.

Figure 8:
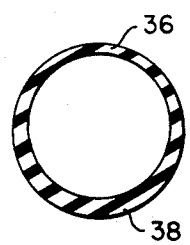
FIG. 8 is a cross-sectional illustration of the tubular portion of a valve element having an eccentric, non-uniform wall thickness.

It should be noted that the tubular element need not be of uniform wall thickness. As suggested at FIG. 8, the cross section of the tubular valving element 20 may be eccentric so that the wall is provided with a minimum region of thickness indicated at 36. With such an arrangement, the element 20 will tend to collapse repeatedly along the relatively thin region of the sidewall. When the eccentric wall configuration, the element 20 preferably is attached or secured in the tubular holder 20 at its thick wall portion 38. Thus, if it is to be retained in the holder 24 by a dab of adhesive, it should be applied at the thick wall portion 38.

Figures 9, 10:
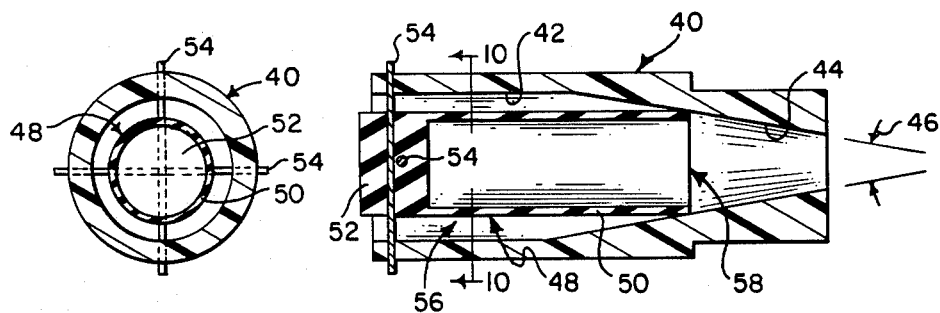
FIG. 9 is a sectional side elevation of a modified embodiment of the invention utilizing a thin walled cylinder and adapted for use with lower pressures and flow rates.
FIG. 10 is a sectional illustration of the device shown in FIG. 9 as seen along the line 10—10 of FIG. 9.

The invention has been described thus far in connection with an embodiment having a relatively thick walled element, better suited for use at higher pressure levels and higher frequency ranges. In some instances, where the differential pressure levels are low and where it may be desired to have higher frequencies, a thin walled valve element may be preferable. FIGS. 9 and 10 illustrate one embodiment of a thin walled valve element. As used herein, the difference between "thick walled" and "thin walled" valve elements is taken with reference to the outer diameter of the tubular valve element. A "thick walled" element is considered to be one in which the wall thickness is greater than one tenth the outer diameter of the tubular element. A thin walled element is considered to be one in which the wall thickness is less than one tenth of the outer diameter of the valve element.

As illustrated in FIGS. 9 and 10, the holder and sealing arrangement are somewhat different than with the thick walled devices. As illustrated in FIGS. 9 and 10, the valve holder 40 does not have a shoulder corresponding to the shoulder 28 in FIG. 2. Rather, the interior of the holder 40 includes an enlarged inlet bore portion 42 which leads and changes to a tapering bore 44 which leads to the outlet of the device. The tapering cone angle of the tapered bore 44 is slight, and lies within the region of approximately four to ten degrees as suggested at the angle 46 in FIG. 9 (exaggerated for clarity of illustration). Additionally, it should be noted that although FIG. 9 discloses an arrangement in which the tapered wall 44 extends fully to the outlet end of the holder 40, the outermost end of the bore, downstream of the thin walled valve element 44, need not be tapered. It is of primary importance, however, that there be a taper at the sealing region where the downstream end of the valve element 48 meets and engages with the tapered wall 44, as described below.

The thin wall valve element 48 may be of similar construction to the previously described elements except that the tubular sidewall 50 is a "thin walled" element. The upstream, closed end 52 of the element 48 may be of a thicker construction, as indicated. In the thin walled embodiment of the invention, the valve element 48 preferably is retained in place by an appropriate holding device at the closed, upstream end 52 of the valve element 48. In the somewhat diagrammatic embodiment of FIGS. 9 and 10, the valve element is shown as being held in place by a pair of cross pins 54 which pass through the enlarged closed end 52 of the valve element and are held in place by the peripheral wall of the holder 40. The pins 54 are arranged to hold the valve element centrally within the passage of the holder 40, thereby defining annular flow passage 56 between the valve element 48 and holder 40. It should be noted that cross pins 54 have been used primarily for illustration purposes and that other techniques for holding the valve element in place in the holder 40 may be employed. For exampler, spider-like devices engageable between the upstream, closed end of the valve and the holder 40 also may be employed, the object in each being to retain the device by its upstream, closed end while providing a flow passage between the valve element and the holder 40. It may be noted further that where the valve device 48 is held in the holder 40 by its upstream, closed end, that completely prevents the possibility of axial collapse of the device which results in other freedoms of design, particularly with configuration of the upstream, closed end of the device.

The clearance required of the flow path 56 is a minimum of one tenth the outer diameter of the valve element. I have found that a preferable length for the thin walled portion of the valve element 48 is of the order of twice the outer diameter of the valve element 48.

The valve element 48 and holder 40 are arranged so that the downstream, open end 58 of the valve member 48 is engageable with a tapered region of the flow passage 44. The valve element 48 and holder 40 are arranged so that with the outer end of the valve member 48 in its expanded, relaxed configuration, a circular band about the periphery of the open end of the valve element will bear against and contact a circular portion of the tapered bore 44. The contacting circular portions define a seal. The sealing band may be disposed at the very outer portion of the open end of the tube or may be disposed slightly inwardly. It may be noted that in most instances, the tube 48 does not have to be formed in a tapered configuration to conform precisely with the tapered bore 44 because the relatively thin walled, flexible, elastic nature of the tube helps it to conform in a sealing relation to the tapered bore 44. However, in the event that it is desired to have a high precision device, in which the width of the sealing band is substantially greater than that resulting from the mating of a tubular valve in conical seat, the valve element may be molded so that its outer free end is tapered, to conform precisely to the configuration of the conical bore 44.

Operation of the thin walled device is substantially the same in principle as that described above in connection with the thick walled device. The valve element incorporates a snap action or toggle-like action when opening, thereby to provide it with a substantially instantaneous opening characteristic as described previously.

Figure 11:
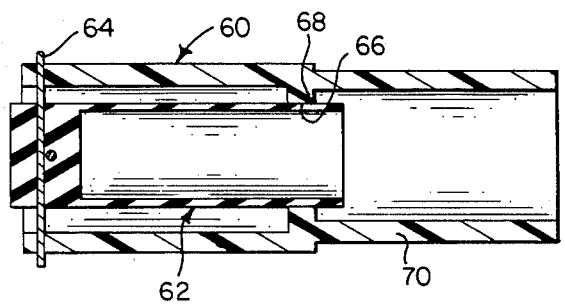
FIG. 11 is an illustration of another modified embodiment of the device.

FIG. 11 shows still another embodiment of the invention which may be used with both thick or thin walled valve elements, although it appears to work more reliably and effectively with thin walled elements. In this embodiment, the valve housing 60 and valve element 62 are arranged to support the valve element by its closed, upstream end, for example by pins 64, spiders or the like, as was the case in connection with the previously described embodiment. In this embodiment, the circumferential seal between the valve element and valve holder is effected by the circumferential surface of an aperture 66 formed in a radially, inwardly extending wall 68 integral with the holder 60. The valve element 62 is dimensioned with respect to the other elements of the holder 60 and, particularly, the apertured wall 68 so that the open end of the valve element 62 protrudes through the aperture 66. The aperture 66 is dimensioned to receive the circumference of the valve element 62 in a snug fit, thereby to effect normally a seal between the valve and sealing surface 66. The forwardmost free, open end of the valve element 62 protrudes somewhat beyond the bottom wall 68 and may be surrounded by an extension wall 70 formed integrally with the holder 60. The extension wall 70 may be considered as the equivalent of element 26 and the embodiment shown in FIG. 2. The radial clearance in the annular passageway between the valve element 62 and housing 60 is of the order of one tenth of the outer diameter of the valve element 62. Preferably, the length of the tubular element extending between the closed end of the valve element 62 to the upstream surface of the wall 68 is approximately twice the outer diameter of the element 62. The extent to which the outer open end of the valve element projects downstream beyond the wall 68 is approximately equal to half the outer diameter of the valve element.

It should be noted further that while the device is intended to be used over a wide range of fluid pressures at the inlet side of the device, it also may be operated by applying negative pressures to the outlet end. Thus, the device may operate in a pulsating mode by connecting the outlet end 16 to a vacuum, thus causing a pressure differential to exist across the valve element 20 which will cause the valve element to operate and pulsate as described above.

The specific manner in which the device may be connected in a fluid flow system may vary depending on the precise use and environment in which the pulsatile device is to be employed. For example, the inlet may be connected by a tube directly to a conventional faucet, as might be desirable in a portable dental hygiene system. Another system, illustrated diagramatically in FIG. 12 is useful in a surgical environment, for example, to dispense sterile irrigation solution to a surgical field. Such use of the invention may include a pressurizable container 80 which has the irrigation solution 82 in it as shown or contained in a flexible bag. The container may be maintained under pressure by gas under pressure such as air or nitrogen, which are commonly available in operating rooms or the like. The pressurized irrigation solution is connected by a tube 84, through a throttle valve 86, to the inlet 14 of the device. The outlet of the device may be connected to a detachable nozzle 88 which defines the shape of the outlet jet, such as in a fine or coarse spray or a direct jet as desired. In that regard, the device lends itself to easy variation in the shape of the jet by simply changing nozzles. The device is compact and the housing 10 itself may serve as a handle by which the nozzle may be manipulated. The valve 86 may be used to make changes in the fluid flow rate into the housing 10, thereby to impart some additional control over the precise frequency and strength of the emitted pulsed jet.

Figure 13:
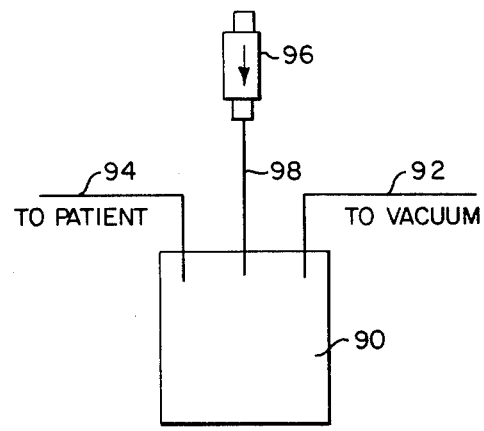
FIGS. 13 and 14 are diagrammatic illustrations of a surgical suction system using the invention in modified modes of operation.

The invention has been described thus far as being usable in a context in which the primary object is to obtain regular pulsations in fluid flow through the device. The invention, however, displays characteristics which enable it to be used in other modes, not necessarily only to generate a steady stream of pulsation. For example, there may be some instances in which the invention may be used in a system where it is desirable only to develop intermittent pulsations or in which it is desired for the valve to be open only for a limited time, and not necessarily to go through repeated opening and closing cycles as is the case with relatively steady pulsations. For example, the characteristic of the device by which it opens at a higher trigger threshhold and closes at a lower reset threshhold may be used advantageously in a suction or vacuum limiting device, for example of the type which is used in surgical suction cannisters for applying suction to a patient's wound, or body cavity. FIG. 13 illustrates diagrammatically a system in which the present invention may be employed, and includes a suction cannister 90 connected to a vacuum source by a line 92 and also connected to the patient by a line 94. A valve, indicated diagrammatically at 96, may be connected to the cannister 90 directly or by a line 98 so as to limit the extent of vacuum which may be developed in the cannister 90 and thereby applied to the patient. The precise manner of operation of the device 96 may depend on the particular requirements for the patient. For example, there may be some instances in which it is desired to have a pulsed vacuum applied to the patient, in which case the device 96 is selected to have the particular pulsation characteristics desired. Alternately, it may be desirable to utilize the characteristics of the device 96 solely to limit the maximum extent of vacuum which is available, in which case the device 96 should be selected as to have parameters which will cause it to open when the vacuum reaches a predetermined triggering level and to close when the pressure differential across the device 96 drops to its reduced reset level.

Figure 14:
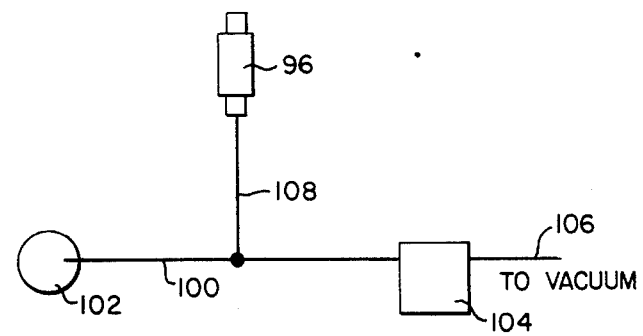

FIG. 14 illustrates a related, but alternate mode of operation for the device used in connection with a closed wound drainage system. In this system, the drainage tube 100 leaves from the wound drainage cite 102 to a collection cannister 104 which, in turn, is connected by a line 106 to a vaccum source. It may be desirable in a system such as this to have periodic vacuum pulsations in the system in addition to assuring that the vacuum developed within the closed wound will not exceed predetermined limitations. To that end, the device 96 may be connected by a line 108 to the drainage line 100. Again, the particular pulsation parameters of the device 96 are selected in accordance with the manner in which the device is to be used. It may be noted that in systems such as the type described in FIGS. 13 and 14, it may not be necessary to utilize a housing for the valve holder. Rather, in some instances, it may be sufficient simply to connect the holder to the system, with the closed end of the valve element being exposed to the atmosphere.

From the foregoing embodiments of the invention, it will be appreciated that among the characteristics of the device is that it provides a check valve function, by preventing reverse flow through the holder. Any back pressure developed downstream of the valve element will not tend to open the seal between the valve element and the holder but, instead, will tend to increase the effectiveness of the seal. Moreover, this check valve feature is incorporated in a device in which the valve element is normally biased in a closed configuration by its resilience and cooperation with the holder.

The device also may be utilized so as to be normally open to permit flow as long as the flow remains at a predetermined rate through the device. With the present invention, if the pressure differential does not drop to the reset level, the valve will not pulsate but, instead, will remain open for as long as that condition continues. Thus, the valve may be used in an opposite mode than that described above, to keep a flow passage open as long as the pressure in the passage is maintained at a sufficiently high level.

It should be understood that the foregoing description of the invention is intended merely to be illustrative of the structure and principles thereof and that other modifications, embodiments and uses for the invention may be apparent to those skilled in the art without departing from its spirit.

Having thus described the invention, what I desire to claim and secure by Letters Patent is:

1. A fluid flow control device comprising:
   a housing having an inlet, an outlet and defining a fluid flow path from the inlet to the outlet;
   a flexible, resilient valve means located within the housing along the flow path for normally obstructing the flow path to preclude flow through the outlet, said valve means comprising a hollow, cylindrical resilient and flexible member having a closed end and open end, said member having greater resistance to axial collapse than to radial collapse;
   said valve means further comprising a cylindrical holder adapted to receive the valve member, at least a portion of the open end of the valve member being disposed within the cylindrical holder with the closed end protruding out of the holder, thereby exposing a portion of the peripheral cylindrical surface of the valve member, at least part of that portion of the cylindrical member which is disposed within the holder effecting a seal between the inner cylindrical surface of the holder and the outer cylindrical surface of the open end of the valve member;
   said valve means being constructed and arranged to shift to an open position in response to a triggering pressure differential of a first magnitude across the valve means, and to return to its obstructing position in response to a drop in said pressure differential to a second magnitude which is less than that of said first magnitude;
   said valve means being constructed and arranged to define a toggle action when shifting from its obstructing to its open configuration, said toggle action being effective to substantially instantaneously shift said valve means from said obstructing to said open position;
   the length of the valve member being approximately double the length of the holder.

2. A device as defined in claim 1 wherein the valve member is constructed and arranged so as to be collapsible along its cylindrical sidewall and in a radial direction, under the influence of a pressure which is a fraction of that required to collapse the valve member axially.

3. A device as defined in claim 2 wherein the valve member is formed in a single, integral piece and in which the closed end is molded integrally with the tubular member and defines a closed end portion.

4. A device as defined in claim 1 wherein the length of the valve member which is received within the holder is not substantially greater than twice the inner diameter of the valve member.

5. A device as defined in claim 1 wherein the valve means is constructed and arranged to be shiftable to an open position only in response to a pressure differential in one direction.

6. A fluid flow device for generating pulsatile flow comprising:
   a housing having an inlet, an outlet, and defining a fluid flow path from the inlet to the outlet;
   flexible, resilient valve means located within the housing along the flow path for normally obstructing the flow path to preclude flow through the outlet;
   said valve means being constructed and arranged to shift between open and obstructing positions in response to changes in the pressure differential between a higher pressure upstream of the valve means and a lower pressure downstream of the valve means;
   said valve means being further constructed and arranged to shift to an open position in response to a triggering pressure differential of a first magnitude across the valve means, and to teturn to its obstructing position solely under the influence of its resilience in response to a drop in the pressure differential across the valve means to a second magnitude which is less than said first magnitude;
   whereby said valve means will oscillate between open and obstructing positions in response to a fluid pressure at the inlet sufficient to create a pressure differential of said first magnitude, said oscillation causing pulsatile flow at the outlet;
   said valve means further comprising a hollow, cylindrical resilient and flexible member having a closed end and an open end, said member having greater resistance to axial collapse than to radial collapse;
   a cylindrical holder adapted to receive the valve member; at least a portion of the open end of the valve member being disposed within the cylindrical holder with the closed end protruding out of the holder, thereby exposing a portion of the peripheral cylindrical surface of the valve member;
   at least part of that portion of the cylindrical member which is disposed within the holder effecting a seal between the inner cylindrical surface of the holder and the outer cylindrical surface of the open end of the valve member;
   the cylindrical wall of the valve element including a weakened region extending longitudinallly of the element;
   the inner diameter and outer diameter of the cylindrical section of the tubular valve member being located eccentrically thereby defining a longitudinally extending narrowed wall portion for the valve member.

* * * * *